United States Patent [19]

Alexandratos

[11] Patent Number: 5,256,808
[45] Date of Patent: Oct. 26, 1993

[54] SYNTHESIS OF TETRAALKYL VINYLIDENE DIPHOSPHONATE MONOMER

[75] Inventor: Spiro D. Alexandratos, Knoxville, Tenn.

[73] Assignee: The University of Tennessee Research Corp., Knoxville, Tenn.

[21] Appl. No.: 985,974

[22] Filed: Dec. 4, 1992

[51] Int. Cl.$^5$ ................................................. C07F 9/40
[52] U.S. Cl. ..................................... 558/142; 558/161
[58] Field of Search .................................. 558/142, 161

[56] References Cited

U.S. PATENT DOCUMENTS 3,686,290  8/1972  Carroll .
4,939,284  7/1990  Degenhardt ........................ 558/142

FOREIGN PATENT DOCUMENTS 1204967  5/1967  United Kingdom .

OTHER PUBLICATIONS

Charles R. Degenhardt & Don C. Burdsall, "Synthesis of Ethenylidenebis (phosphonic acid) and Its Tetraalkyl Esters", *J. Org. Chem.* 1986, 51, 3488–3490.
Lehnert, W. *Tetrahedron* 1974, 30, 301–305.

*Primary Examiner*—Mary C. Lee
*Assistant Examiner*—Michael G. Ambrose
*Attorney, Agent, or Firm*—Reinhart, Boerner, Van Deuren, Norris & Rieselbach

[57] ABSTRACT

A method of making a monomer of tetraalkyl vinylidene-1, 1-diphosphonate. The monomer is manufactured by combining an aqueous secondary amine solution with a formaldehyde and a tetra (alkyl) methylene diphosphonate. The resulting mixture is maintained at a pH above about 6 and refluxed for two hours to enable reaction to produce the monomer of tetraalkyl vinylidene-1, 1-diphosphonate. The product monomer is then purified to produce the final end product.

23 Claims, 2 Drawing Sheets

SYNTHESIS OF TETRAALKYL VINYLIDENE DIPHOSPHONATE MONOMER

This invention was made with government support under Contract No. 00222401 awarded by The Department of Energy. The government has certain rights in this invention.

The present invention is directed generally to a method of preparing a monomer of tetraalkyl vinylidene-1, 1-diphosphonate. More particuarly, the invention is directed to a method of preparing in a few hours of reaction time the monomer of tetraalkyl vinylidene-1, 1-diphosphonate.

The monomer of tetraalkyl vinylidene-1, 1-diphosphonate has a number of important uses including the manufacture of ion exchange resins, polymeric flame retardants and pharmaceutical applications. Conventional methods of producing this monomer have included (1) thermal dehydration of tetrasodium (1-hydroxyethylidene) bis (phosphonate) at high temperatures and (2) a two-step process as set forth in U.S. Pat. No. 4,939,284 involving the base catalyzed reaction of a methylenebis (phosphonate) ester with a paraformaldehyde followed by addition of an acid catalyst to catalyze elimination of alcohol from the reaction product. The first method, however, has the disadvantage of requiring precise temperature control during the dehydration step and a lengthy, time-consuming purification process. The second method avoids these problems, but the reaction time typically requires ten days to go to seventy percent completion for the tetraisopropyl ester form. In addition, this procedure requires use of an alcohol solvent which complicates processing conditions.

It is therefore an object of the invention to provide an improved method of making a monomer of tetraalkyl vinylidene-1, 1-diphosphonate.

It is another object of the invention to provide a novel method of rapidly forming a monomer of tetraalkyl vinylidene-1, 1-diphosphonate.

It is a further object of the invention to provide an improved method of forming a tetraalkyl vinylidene-1, 1-diphosphonate using an aqueous solvent.

It is yet another object of the invention to provide a novel method of producing a tetraalkyl vinylidene-1, 1-diphosphonate by simultaneously reacting an aqueous solution of formaldehyde with all other aqueou soluble components.

It is still an additional object of the invention to provide an improved method of producing tetraalkyl vinylidene-1, 1-diphosphonate without need for a separate elimination step for intermediates or use of an acid catalyst.

Other objects and advantages of the invention, together with the manner of operation, will become apparent upon reference to the following Detailed Description, Examples and appended c aim along with the drawing described below:

DETAILED DESCRIPTION OF A PREFERRED EMBODIMENT

Figure 1:
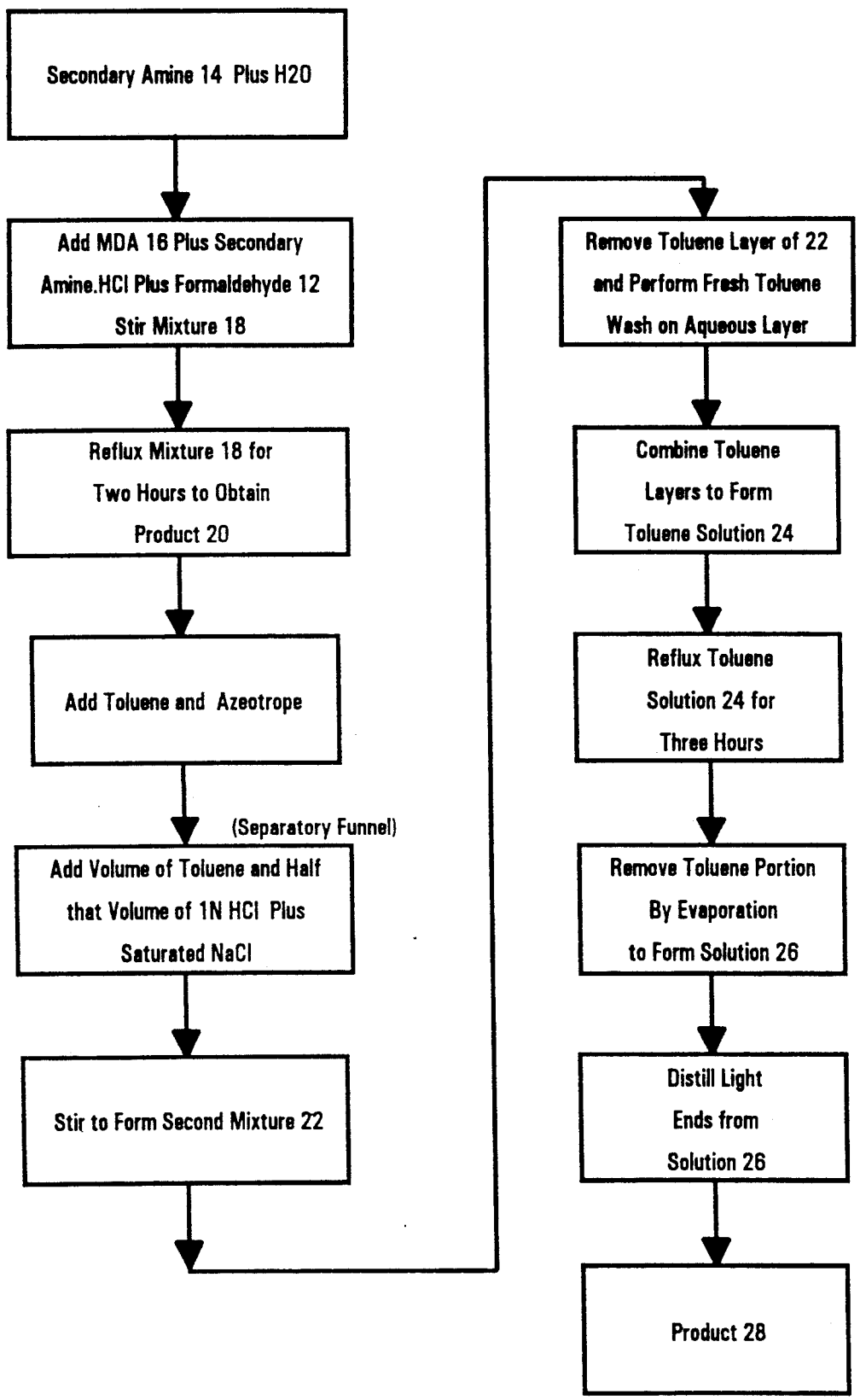
FIG. 1 illustrates as a flow diagram one method of the invention.

A preferred method of manufacturing a monomer of tetraalkyl vinylidene-1, 1-diphosphonate in accordance with the invention is illustrated in FIG. 1. Reactants 10 are accumulated from conventional supply sources, and the reactants 10 include a first reactant 12 of formaldehyde, such as, for example, formalin, paraformaldehyde or trioxane. A second reactant 14 includes a secondary amine, such as, for example, a dipropylamine, dimethylamine or diethylamine. A third reactant 16 includes a tetra (alkyl) methylene diphosphonate (MDA), such as, for example, tetra (methyl), or (ethyl), or (propyl) or (isopropyl) methylene diphosphonate.

In this embodiment the reactants 10 are combined by dissolving the amine into water, the MDA and formalin is added and a resulting mixture 18 is stirred. The pH is monitored to initilize the pH above about 6 in order to allow the reaction to proceed (during which pH will vary in accordance with the reaction). While a most preferred initial pH range is 7.35–7.4, any pH above 6 (and up to 14) will suffice. To control initial pH one can add a secondary amine·HCl, (or other such conventional acidic formulations) with the formalin. Thus, one can add formalin, diethylamine and diethylamine HCl and MDA. The preferred ratio of formalin to diethylamine and diethylamine HCl to MDA is about 3.2:0.6:1:1. This can be compared to the preferred basic constituent ratios of formalin:dipropylamine:MDA of about 3.2:1.8:1.

The aqueous mixture 18 is placed into a container, such as a heavy walled flask, and closed with a stopper. The mixture 18 is refluxed for about one to two hours to achieve a product 20. Under these most preferred conditions, increased reflux time beyond about two hours does not substantially affect the yield.

In a most preferred form of the invention, a higher purity product can be obtained by purifying the product 20. The product 20 is placed in a separatory funnel. In this preferred method after refluxing the mixture 18 for about one to two hours, but before adding toluene to form the second mixture 22, a toluene and azeotrope is added to the product 20. A volume of toluene and half the toluene volume of 1 N HCl (and also preferably including NaCl) is then added to form the second mixture 22. This second mixture 22 is stirred, and the contents are allowed to settle.

The toluene layer of the second mixture 22 is removed, and a fresh toluene wash is performed on the aqueous layer. The two toluene layers are then combined to form toluene solution 24. The combined toluene solution 24 is added to a one-neck flask, and a Dean-Stark trap and condenser are added to the flask. The toluene solution 24 is refluxed for about three hours, emptying the Dean-Stark trap enough (usually several times) until only toluene is being distilled over. The toluene portion is then removed by using a rotary evaporator by heating the toluene solution 24° to 60° C.

The light end products are then distilled off a remaining solution 26 under vacuum conditions (0.05–0.10 torr). Distillation is then stopped when the temperature reaches 104° C. (typically requiring about an hour of time). The flask is then opened to the atmosphere when the remaining solution cools to 25° C. A remaining product mix 28 contains monomeric tetraalkyl vinylidene-1, 1-diphosphonate and MDA in the ratio of about 81:19 or greater and with a product yield of about 90%.

Figure 2:
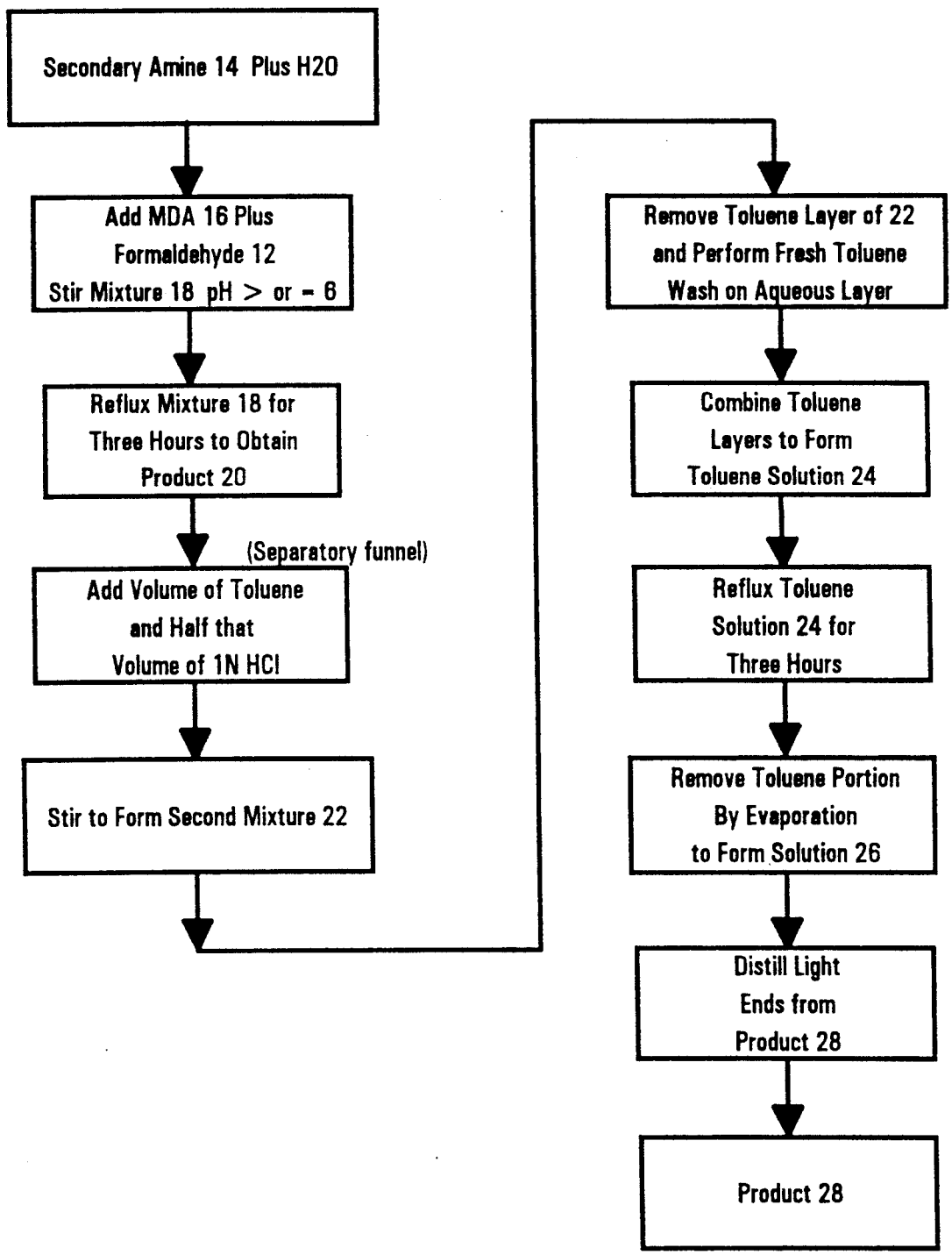
FIG. 2 shows as a flow diagram another method of the invention.

In a second form of the invention, as shown in FIG. 2, the initialized pH in the second step can be achieved by adding a concentrated acid, such as HCl, to establish the pH at or above a value of 6. In the third step the mixture 18 is refluxed for about three hours to achieve the product 20. Extending the reflux time beyond about three hours does not substantially affect the yield.

As in the preferred process of FIG. 1, further purification steps can be used to improve the product purity. As shown in FIG. 2 a volume of toluene and half that volume of 1 N HCl is added to the product 20 to form a second mixture 22. Further processing steps are substantially the same as in the process of FIG. 1. The remaining product mix contains monomeric tetraalkyl vinylidene-1, 1-diphosphonate and MDA in the ratio of about 7:3 and greater.

The following nonlimiting examples illustrate several methods of preparation of the tetraalkyl vinylidene-1, 1-diphosphonate.

EXAMPLE 1

Into a 200 mL heavy-walled flask, place 18.0 g dipropylamine, 13.2 g $H_2O$, and 13.3 mL concentrated HCl. Add the HCl slowly due to the exothermicity of the reaction. Then add 32.1 g tetraisopropyl methylene diphosphonate (MDA) and 25.0 g formalin. Stir and take the pH. Add enough amine (usually 3 mL to give a final pH of 7.35-7.4. Close the flask with a teflon stopper, reflux for three hours and cool to 25° C.

Place the solution into a separatory funnel, adding 50 mL 1 N HCl and 100 mL toluene. Mix, allow to settle and collect the toluene layer. Repeat the wash of the aqueous layer with an additional 100 mL toluene. Combine the toluene layers and reflux for three hours in a flask with an attached condenser and Dean-Stark trap. Cool and remove the toluene with a rotary evaporator. Distill off the light ends under vaccuum (0.05-0.10 torr), and stop the distillation once the temperature is at 104° C. (one hour). Cool the product. Twenty-two grams are isolated in 97% purity with a vinylidene:MDA ratio of 70:30.

EXAMPLE 2

As in Example 1 above, except the pH is adjusted to 6.85; a resulting vinylidene:MDA ratio is 22.7:72.3.

EXAMPLE 3

As in Example 1 above, except with no added HCl (pH=14); get vinylidene:MDA ratio is 63.6:36.4. This was repeated for pH values between 8 and 14 in increments of about 1.0. The vinylidene:MDA ratio steadily improved upon reduction below pH of 14 until reaching pH's of 6-7 as shown in other examples.

EXAMPLE 4

As in Example 1, except use 40% aqueous dimethylamine solution, a 5:2:1 formalin:amine:MDA initial ratio, and a pH of 6.86; a resulting vinylidene:MDA ratio is 3.4:96.6.

EXAMPLE 5

As in Example 4, except with pH adjusted to 7.21; a resulting vinylidene:MDA ratio is 48.6:51.4.

EXAMPLE 6

As in Example 4, except with pH of 7.43; a resulting vinylidene:MDA ratio is 56.3:43.7.

EXAMPLE 7

As in Example 4, except with pH of 7.73; a resulting vinylidene:MDA ratio is 67.4:32.6.

EXAMPLE 8

As in Example 1, except with paraformaldehyde:diethylamine: MDA in a 5:2:1 ratio and no water as solvent; a vinylidene:MDA ratio of 54.2:45.8 and a 57% yield.

EXAMPLE 9

As in Example 8, except with a 2:2:1 ratio and a 16.5 hour reaction time; get vinylidene:MDA ratio of 40:60 and 42% yield.

EXAMPLE 10

The same steps as Example 1 were carried out except a secondary amine complexed with HCl was added along with the formalin making unnecessary the control of pH using HCl in step two of FIG. 1. The ratio of formalin to diethylamine to diethylamine HCl to MDA is preferably about 3.2 to 0.6 to 1 to 1. The diethylamine can be any quantity from 0.1 to 1.0 moles, most preferably 0.6 moles. For 0.4 moles, the yield is 90.3% (MDA/monomer=33/67); for 0.5 moles, the yield is 85.3% (MDA/monomer=25/75); for 0.9 moles, the yield is 54% (MDA/monomer=38/62).

EXAMPLE 11

The same procedure as Example 10 was followed except the quantity of diethylamine.HCl was varied from 0.1-5.0 moles, the most preferred being 1.0 moles. At 0.6 moles, the yield is 79.8% with MDA/monomer=20/80. AT 0.8 moles, the yield is 83.1% with MDA/monomer=20/80.

EXAMPLE 12

The same procedure as Example 10 was followed except for the quantity of formalin used was varied from 1.0-10.0 moles (most preferably is 3.2 moles). At 4.0 moles the yield is 82.5% with the MDA/monomer=21/79. At 5.0 moles, the yield is 80.6% with the MDA/monomer=23/77.

EXAMPLE 13

The same procedure as Example 10 was followed, but all quantities of components were increased by the same molar percentage except for the MDA. The product results are substantially insensitive. If increase quantities by 10%, the yield is 84.2% with MDA/monomer—22/78. If quantities are increased by 40%, then the yield is 76% with an MDA/monomer ratio of 19/81.

EXAMPLE 14

The same procedure as in Example 10 was followed except a variety of secondary amines and secondary amine salts were used. Dipropylamine (0.1-1.0 moles) was combined with dimethylamine.HCl in the ratio of, for example, dipropylamine at 0.6 moles and dimethylamine.HCl at 1 mole. This yields 83.9% with the ratio of MDA/monomer (VDPA) being 34/66.

For diethylamine (0.1-1.0 moles) was combined with dimethylamine·HCl in the preferred ratio of diethylamine at 0.6 moles to dimethylamine·HCL at 1 moles. This yields 86.7% with an MDA/VDPA monomer ratio of 25/75.

For dibutylamine (0.1–1.0 moles) was combined with dimethylamine·HCl in the ratio of 0.6 to 1.0, yielding 58% product. The MDA/VDPA monomer ratio is 33/67.

EXAMPLE 15

The same procedure as in Example 10 was followed with the effect of temperature on yield and MDA/monomer (VDPA) evaluated. The ratio of formalin to diethylamine to dimethylamine.HCl to MDA was 3.2 to 0.1 to 1.0 to 1.0. For two hours at reflux temperatures the yield was 80.1% with a ratio of 24/76 for MDA/monomer. For two hours at 64° C. the yield was 78.2% with a ratio of 43/57 for MDA/monomer. For two hours at 50° C. the yield was 87.9% with a ratio of 67/23 for the MDA/monomer.

EXAMPLE 16

A most preferred form of the first embodiment of the invention was prepared as follows:

A. Reactant Charge Was Prepared
1. Obtain a 2 liter reaction vessel with stirrer;
2. Add 34.4 grams (0.314 moles) of diethylamine hydrochloride to the vessel;
3. Add 81.5 grams (75 ml, 1.00 moles) of formalin and stir until diethylamine hydrochloride is completely dissolved;
4. Add 108 grams (102 ml, 0.314 moles) of MDA and stir several minutes until gradient disappears;
5. Add 13.8 grams (20 ml, 0.19 moles) of diethylamine. (The temperature usually rises to 35° C. from 25° C. after the diethylamine is completely mixed).

B. Reflux Mixture:
1. Seal the vessel using a suitable accumulator to allow for a volume increase as temperature increases and heat the mixture under reflux@100° C. for 2 hours while stirring; and
2. Cool the vessel to room temperature (if handling before next step is necessary).

C. Azeotrope Mixture Preparation:
1. Add 628 ml of toluene. The mixture shows two separate phases. The top layer, toluene, is clear and the bottom layer, aqueous, is yellowish-brown;
2. Connect a Dean-Stark trap (or equivalent) to collect water, toluene and coarse contaminant;
3. Stir and rapidly heat the system (begins around 90° C. and then slowly rises to 112° C. when water is completely removed) to reflux azeotrope water with toluene from the mixture. The azeotroped solution which has been treated shows two phases (the lower layer is water and the upper layer is toluene) collected in the trap. Continue heating until water ceases to distill over. The total volume of water collected should be approximately 62.8 ml;
4. Discard the water collected along with residual toluene floating in the trap; and
5. A yellowish-brown residue is present on the bottom of the product flask. Cool the material while agitating to suspend and disperse this residue while it is solidifying.

Purification Steps:
A. Extraction of Product:
1. Transfer the above product to a suitable size separatory funnel, and then add 157 ml of NaCl saturated 1 N HCl$_{(aq)}$ solution*.
2. Agitate the system vigorously until fully mixed, and then allow system to settle until upper toluene layer becomes clear (usually takes 5–10 minutes).
3. Drain and collect lower layer (contains aqueous phase and some solids) from the bottom;
4. The toluene phase remaining in the separatory funnel is collected for further treatment;
5. Pour the aqueous solution and solid mixture obtained from step 3 above back to the separatory funnel and then add 314 ml of fresh toluene. The mixture is treated by the same procedures as purification steps 2, 3 and 4 above; and
6. Discard aqueous phase and solids mixture (the total volume is about 220 ml). * 200 ml of 1 N HCl$_{(aq)}$+50 g of NaCl. The mixture is stirred until NaCl is completely dissolved before using.

B. Second azeotrope steps:
1. The toluene solutions obtained from purification steps A.4 and 5 above are mixed and then azeotroped under reflux (the temperature should be around 110° C.±5° C.) for 3 hours in the same apparatus used before. Discard the first 314 ml solution collected in the trap (contains mostly toluene and a small amount of water) and then continue to heat the solution at reflux until the three hours have elapsed; and
2. After the system is cooled to 25° C. (room temperature), the solution is filtered and is then ready for vacuum distillation.

C. Vacuum Distillation:
1. Distill most of the toluene off under vacuum (10 mmHg) at 70° C. (starts from 50° C. and then rises to 70° C. with a rate of about 1° C./min) for 1 hour;
2. Distill the remaining toluene and impurities off under high vacuum (0.1 mmHg) at 105° C. for 30 minutes*; and
3. Turn off the heat and allow the system to cool to room temperature. For safety purposes, do not release vacuum until the product is fully cooled.

* Note that other vacuum experiments show that a yield ratio of monomer to tetra (alkyl) methylene diphosphonate is up to about 9:1 for very high vacuum processing.

Ninety-six grams (89.8% yield) of monomer solution in a MDA:VDPA and a ratio of 19/81 is obtained through this above described procedure.

What is claimed is:

1. A method of making a monomer of tetraalkyl vinylidene-1, 1-diphosphonate, comprising the steps of:
   (a) combining a secondary amine, a formaldehyde and a tetra (alkyl) methylene diphosphonate to form a first aqueous mixture;
   (b) maintaining the pH of said aqueous mixture above about 6 while reaction occurs in said mixture; and
   (c) refluxing said aqueous mixture to obtain a refluxed product of said monomer of tetraalkyl vinylidene-1, 1-diphosphonate.

2. The method as defined in claim 1 wherein said secondary amine is first combined with water to form an aqueous amine solution and said amine solution is next mixed with said formaldehyde and said tetra (alkyl) methylene diphosphonate to form said first aqueous mixture.

3. The method as defined in claim 1 wherein said tetra (alkyl) methylene diphosphonate is selected from the group consisting of tetra (methyl), tetra (ethyl), tetra (propyl) and tetra (isopropyl) methylene diphosphonate.

4. The method as defined in claim 1 wherein said secondary amine comprises at least one of dipropylamine, diethylamine and dimethylamine.

5. The method as defined in claim 1 wherein said formaldehyde is selected from the group consisting of formalin, a paraformaldehyde and trioxane.

6. The method as defined in claim 1 wherein said pH is about 7.35–7.40.

7. The method as defined in claim 1 wherein said step (c) is performed in about two hours time.

8. The method as defined in claim 1 further including a purification step for processing said reflexed product.

9. The method as defined in claim 8 wherein said purification step comprises:
   (1) adding toluene and acid to said refluxed product to form a mixture;
   (2) refluxing said mixture of toluene, acid and said refluxed product; and
   (3) evaporating and distilling unwanted portions of said refluxed mixture to form a purified monomer of tetraalkyl vinylidene-1, 1-diphosphonate.

10. The method as defined in claim 9 wherein said monomer is isolated with about 97% purity.

11. The method as defined in claim 9 wherein said monomer has a vinylidene:MDA ratio range of about 3.4 to 96.6 to 7 to 3.

12. The method as defined in claim 1 wherein said pH ranges from about 6 to 14.

13. A method of making a monomer of tetraalkyl vinylidene-1, 1-diphosphonate, comprising the steps of:
   (a) combining a secondary amine with water to form an aqueous amine solution;
   (b) combining a formaldehyde and a tetra (alkyl) methylene diphosphonate with said aqueous amine solution to form a first aqueous solution;
   (c) adjusting pH of said first aqueous solution to be between about 6 and 14;
   (d) refluxing said first aqueous solution for about 3 hours to form a refluxed product; and
   (e) purifying said refluxed product to produce said monomer.

14. The method as defined in claim 13 wherein said pH is about 6.85 to 7.45.

15. The method as defined in claim 13 wherein said formaldehyde is selected from the group consisting of formalin, paraformaldehyde, and trioxane.

16. The method as defined in claim 13 wherein said tetra (alkyl) methylene diphosphonate comprises at least one of tetra (methyl), tetra (ethyl), tetra (propyl) and tetra (isopropyl) methylene diphosphonate.

17. The method as defined in claim 13 wherein said secondary amine is selected from the group consisting of dipropylamine, diethylamine and dimethlyamine and higher order amines.

18. The method as defined in claim 13 wherein the ratio range of said monomer to said tetra (alkyl) methylene diphosphonate is about from 3.4 to 96.6 to about 7 to 3.

19. The method as defined in claim 13 wherein the upper ratio of said monomer to said tetra (alkyl) methylene diphosphonate is about 9 to 1 if distillation during purification is performed at very high vacuum less than about 0.01 mm Hg.

20. A method of making a monomer of tetraalkyl vinylidene-1, 1-diphosphonate, comprising the steps of:
   (a) combining a secondary amine, a formalin and a tetra (alkyl) methylene diphosphonate to form a first aqueous mixture; and
   (b) refluxing said aqueous mixture to obtain a refluxed product of said monomer of tetraalkyl vinylidene-1, 1-diphosphonate.

21. The method as defined in claim 20 wherein a secondary amine hydrochloride is further added in said step (a).

22. The method as defined in claim 20 wherein said secondary amine comprises about 0.1–1.0 moles.

23. The method as defined in claim 30 wherein said formalin is varied from about 0.1–1.0 moles.

* * * * *